(12) United States Patent
Shalaby et al.

(10) Patent No.: US 9,011,439 B2
(45) Date of Patent: Apr. 21, 2015

(54) SELECTIVELY ABSORBABLE/BIODEGRADABLE, FIBROUS COMPOSITE CONSTRUCTS AND APPLICATIONS THEREOF

(75) Inventors: Shalaby W. Shalaby, Anderson, SC (US); Shawn Peniston, Easley, SC (US); Kimberly A. Carpenter, Pendleton, SC (US)

(73) Assignee: Poly-Med, Inc., Anderson, SC (US)

( * ) Notice: Subject to any disclaimer, the term of this patent is extended or adjusted under 35 U.S.C. 154(b) by 1395 days.

(21) Appl. No.: 11/983,321

(22) Filed: Nov. 8, 2007

(65) Prior Publication Data

US 2008/0119848 A1    May 22, 2008

Related U.S. Application Data

(60) Provisional application No. 60/860,033, filed on Nov. 20, 2006.

(51) Int. Cl.
| | |
|---|---|
| *A61B 17/04* | (2006.01) |
| *A61B 17/56* | (2006.01) |
| *A61L 27/48* | (2006.01) |
| *A61L 27/58* | (2006.01) |
| *C08L 23/06* | (2006.01) |

(52) U.S. Cl.
CPC .............. *A61L 27/48* (2013.01); *A61L 27/58* (2013.01); *C08L 23/06* (2013.01); *C08L 2203/12* (2013.01)

(58) Field of Classification Search
None
See application file for complete search history.

(56) References Cited

U.S. PATENT DOCUMENTS

| | | | | |
|---|---|---|---|---|
| 4,743,257 A * | 5/1988 | Tormala et al. | ............ | 623/23.58 |
| 5,002,551 A * | 3/1991 | Linsky et al. | ................. | 606/151 |
| 5,782,903 A * | 7/1998 | Wiktor | ......................... | 623/1.22 |
| 5,834,113 A | 11/1998 | Shalaby | | |
| 6,069,192 A | 5/2000 | Shalaby | | |
| 6,652,563 B2 | 11/2003 | Dreyfuss | | |
| 6,703,035 B2 * | 3/2004 | Shalaby | ......................... | 424/408 |
| 6,716,234 B2 * | 4/2004 | Grafton et al. | ................. | 606/228 |
| 6,794,485 B2 * | 9/2004 | Shalaby et al. | ............... | 528/354 |
| 7,029,490 B2 | 4/2006 | Grafton et al. | | |
| 7,066,956 B2 | 6/2006 | Schmieding et al. | | |
| 7,077,863 B2 | 7/2006 | Schmieding et al. | | |
| 2004/0224406 A1 * | 11/2004 | Altman et al. | ................. | 435/395 |
| 2004/0265355 A1 * | 12/2004 | Shalaby | ......................... | 424/426 |
| 2004/0267362 A1 * | 12/2004 | Hwang et al. | .............. | 623/13.15 |
| 2005/0149118 A1 * | 7/2005 | Koyfman et al. | ............. | 606/228 |

OTHER PUBLICATIONS

Altman, Biomaterials, 23, 2002.*
Deng, Biomaterials, 23, 2002.*
U.S. Appl. No. 11/886,370, filed Sep. 14, 2007, Shalaby.
U.S. Appl. No. 11/879,357, filed Jul. 17, 2007, Shalaby.
Altman, G.H. et al., "Silk Matrix for tissue engineered anterior cruciate ligaments," Biomaterials, 23, 4131-4141, 2002.

* cited by examiner

*Primary Examiner* — Susan Tran
*Assistant Examiner* — William Craigo
(74) *Attorney, Agent, or Firm* — McNair Law Firm, P.A.; Douglas L. Lineberry

(57) ABSTRACT

A family of selectively absorbable/biodegradable, fibrous composite constructs includes different combinations of biostable and absorbable/biodegradable yarns assembled as initially interdependent, load-bearing components, transitioning to exhibit independent functional properties during in vivo end-use. The family of constructs consists of two groups, one group is made of fiber-reinforced composites of high compliance, absorbable matrices of segmented polyaxial copolyesters reinforced with multifilament yarn constructs, which are combinations of ultrahigh molecular weight polyethylene fibers and at least one absorbable/biodegradable fiber selected from silk fibers and multifilament yarns made from linear segmented, l-lactide copolyesters and poly (3-hydroxyalkanoates, are useful in orthopedic, maxillofacial, urological, vascular, hernial repair and tissue engineering applications. The second group is made of coated and uncoated, warp-knitted mesh constructs for use in hernial, vascular, and urological tissue repair and tissue engineering.

35 Claims, No Drawings

SELECTIVELY ABSORBABLE/BIODEGRADABLE, FIBROUS COMPOSITE CONSTRUCTS AND APPLICATIONS THEREOF

The present application claims the benefit of prior provisional patent application U.S. Ser. No. 60/860,033, filed Nov. 20, 2006.

FIELD OF THE INVENTION

This invention relates to a family of selectively absorbable/biodegradable fibrous composite constructs comprising (1) a group of fiber-reinforced composites which are selectively absorbable/biodegradable by virtue of their unconventional make-up of an absorbable, compliant, segmented polyaxial copolyester matrix mediating the stiffness of a fibrous, reinforcing construct, which is a combination of biostable multifilament or monofilament yarns made of polymers such as ultrahigh molecular weight polyethylene (UHMW-PE), polypropylene, and a polyalkylene terephthalate, with enzymatically degradable fibers and/or hydrolytically degradable fibers; and (2) a second group of coated or uncoated, warp-knitted, selectively absorbable, composite fibrous constructs comprising a combination of (a) one or more absorbable/biodegradable yarn(s), (b) at least one biostable monofilament or multifilament yarn, and (c) an absorbable polyester for surface treating the coated constructs. The two groups of selectively absorbable biodegradable composite constructs are designed to produce devices exhibiting time-modulated strength retention and mass loss profiles, which allow their broad use in orthopedic, maxillofacial, urological, vascular, hernial repair, and tissue engineering applications.

BACKGROUND OF THE INVENTION

The exceptionally high-strength and modulus of ultrahigh molecular weight polyethylene (UHMW-PE) fibers and their relatively low density compared with carbon, polyaramide, and metallic fibers has led to their preferred use in a number of high performance textile constructs and industrial, fiber-reinforced composites of thermoplastic and thermosetting polymers. Among the key reasons for their growing use in fiber-reinforced composites is the fact that the UHMW-PE density is about 1 g/cm$^3$; thus, a small weight fraction of the UHMW-PE fibers in these composites provide relatively high volume fractions. Meanwhile, the successful use of UHMW-PE in high-strength textile fabrics and high performance composite applications drew the attention of contemporary medical and bioengineering investigators and inventors. Subsequently, an increasing percentage of the prior art dealing with the use of UHMW-PE fibers pertained to biomedical applications, such as their use (1) in self-reinforced composites, where less than 10 weight percent of fibers resulted in significant increases in the UHMW-PE matrix (U.S. Pat. No. 5,834,113); (2) after chemically activating the surface to increase the adhesion of the UHMW-PE fibers to reinforced traditional matrices of medical significance, such as polymethyl methacrylate and epoxy resins (U.S. Pat. No. 6,069,192); and (3) in combination with other synthetic fibers, namely the non-absorbable polyethylene terephthalate (PET) or the absorbable poly-p-dioxanone (PDS) fibers as orthopedic sutures and allied ligating devices (U.S. Pat. Nos. 7,077,863; 7,066,956; 7,029,490; 6,716,234; 6,652,563). However, investigators who used UHMW-PE fibers or their blends with PET or PDS fibers as orthopedic sutures, ignored a less obvious disadvantage of UHMW-PE that is associated with its exceptionally high modulus, namely, the poor biomechanical compatibility with the cellular components of most biological tissues. And simple blending of UHMW-PE fibers with the high glass transition temperature ($T_g$) PET fibers, does not mediate the overall stiffness and temper of the poor biomechanical compatibility of suture constructs made thereof. Furthermore, using high compliance PDS fibers in a blend with UHMW-PE to form orthopedic sutures with a staged strength retention profile and partial mass loss to encourage early tissue ingrowth to stabilize the remaining long-term UHMW-PE component of the implant can result in a new clinical problem. The latter can be associated with an early loss of PDS strength leading to a premature decrease in the load-bearing capacity of the UHMW-PE-based orthopedic device prior to the conclusion of the critical period for significant bone regeneration, particularly in patients with compromised tissue healing. This prompted the pursuit of the study of a group of fiber-reinforced composites comprising compliant polyaxial copolyesters and at least one biostable reinforcing yarn made of UMWPE polypropylene and a polyalkylene terephthalate, subject of this invention. Of special interest among these composites are the ones based on UMWM-PE yarn, which provide (1) a solution for mediating the effect of UHMW-PE stiffness on living cells through encasing the UHMW-PE-based fiber blends in a highly compliant, absorbable matrix, which presents these cells with a biomechanically compatible surface; (2) substituting the non-absorbable, high $T_g$ PET with a low $T_g$ segmented absorbable copolyester, which does not only impart a higher biomechanical compatibility to the UHMW-PE fiber-based construct, but also allows more timely and prolonged mass loss and strength loss profiles compared to PDS fiber; and (3) natural, highly biocompatible silk fibers as a component of the reinforcing fibrous construct to support natural tissue regrowth and engineering—silk fibers have been described as a useful matrix for tissue engineered anterior cruciate ligaments [Altman, G. H. et al., *Biomaterials,* 23(20), 4131 (2002)].

As discussed above, the concept of combining absorbable and non-absorbable fibers has been applied, to a limited extent, to produce partially absorbable hernial meshes and vascular devices. In addition, the present inventors have described in a recent disclosure, totally absorbable/biodegradable composites comprising at least two fibrous components with distinctly different individual physicochemical and biological properties for use in constructing absorbable/biodegradable medical devices or surgical implants, such as meshes and vascular grafts displaying a gradient in clinically relevant properties (U.S. patent applications Ser. Nos. 11/886,370 and 11/879,357 filed on Sep. 14, 2007 and Jul. 17, 2007, respectively, each of which are hereby incorporated herein by reference in their entireties). However, none of the early prior art and recent disclosures dealt with selectively absorbable/biodegradable, composite constructs comprising combinations of biodegradable and biostable yarns assembled as initially interdependent, load-bearing components transitioning to exhibit independent functional properties during in vivo end-use in degrading environments. And this, in part, prompted the pursuit of a second group of selectively absorbable, specially warp-knitted, composite fibrous constructs with or without an absorbable surface coating.

SUMMARY OF THE INVENTION

This invention deals with two groups (or types) of a family of selectively absorbable/biodegradable, fibrous composite constructs comprising different combinations of absorbable/biodegradable and biostable yarns. And each group is represented by a selectively absorbable/biodegradable, fibrous composite construct comprising less than about 70 percent by weight of at least one biostable and one or more absorbable/biodegradable yarns assembled as initially interdependent, load-bearing components, transitioning to exhibit independent functional mechanical properties during in vivo end-use in degrading environments.

For the first group of constructs, part of this invention deals generally with a selectively absorbable/biodegradable, fibrous composite construct comprising less than about 70 percent by weight or less than about 40 percent by weight of at least one biostable and one or more absorbable/biodegradable yarns assembled as initially interdependent, load-bearing components, transitioning to exhibit independent functional mechanical properties during in vivo end-use in degrading environments, wherein the said fibrous composite construct is part of a fiber-reinforced composite of a biodegradable, segmented, polyaxial copolyester matrix reinforced with a multifilament yarn construct including a biostable yarn of ultrahigh molecular weight polyethylene and at least one absorbable/biodegradable yarn of heterochain polymer, and wherein the weight percentage of the matrix in the fiber-reinforced construct varies from about 10 to 40. More specifically, the weight percentage of the matrix in the fiber-reinforced construct varies from about 15 to 50.

In a specific aspect of this part of the invention dealing with a fiber-reinforced composite comprising a matrix comprising a biodegradable, segmented, polyaxial copolyester and a reinforcement within the matrix, the reinforcement comprising a multifilament yarn of ultrahigh molecular weight polyethylene and at least one absorbable/biodegradable yarn comprising a heterochain polymer, the biodegradable, segmented polyaxial copolyester matrix is formed of an amorphous, polyaxial, polymeric initiator end-grafted with a mixture of ε-caprolactone and at least one cyclic monomer selected from the group consisting of l-lactide, dl-lactide, glycolide, and trimethylene carbonate, which forms crystallizable terminal segments. Meanwhile, the amorphous, polymeric initiator is formed by the ring-opening polymerization of trimethylene carbonate in the presence of a catalyst, preferably stannous octanoate, and a monocentric polyfunctional initiator selected from the group consisting of triethanolamine, trimethylol-propane, and pentaerythritol. Alternatively, the amorphous, polymeric initiator is formed by the ring-opening polymerization of a mixture of trimethylene carbonate and at least one monomer selected from p-dioxanone, ε-caprolactone, and 1,5-dioxepan-2-one.

In another specific aspect of this part of the invention dealing with a fiber-reinforced composite comprising a matrix comprising a biodegradable, segmented, polyaxial copolyester and a reinforcement within the matrix, the reinforcement comprising a multifilament yarn of ultrahigh molecular weight polyethylene and at least one absorbable/biodegradable yarn comprising a heterochain polymer, the absorbable/biodegradable yarn is formed of least one polymer selected from the group consisting of silk protein, a linear, segmented l-lactide copolyester, and a poly(3-hydroxyalkanoate). Specifically, the absorbable/biodegradable yarn may be formed of (1) a silk protein in the form of degummed, white Brazilian raw *Bombyn mori* silkworm fibers; (2) a segmented copolymer of l-lactide and at least one monomer selected from glycolide, ε-caprolactone, trimethylene carbonate, p-dioxanone, and a morpholinedione; and/or (3) a poly(3-hydroxyalkanoate) selected from poly(3-hydroxybutyrate) and poly(3-hydroxybutyrate-co-3-hydroxyvalerate).

In a clinically significant aspect of this part of the present invention dealing with a fiber-reinforced composite comprising a matrix comprising a biodegradable, segmented, polyaxial copolyester and a reinforcement within the matrix, the reinforcement comprising a multifilament yarn of ultrahigh molecular weight polyethylene and at least one absorbable/biodegradable yarn comprising a heterochain polymer, the composite is in the form of an orthopedic device such as orthopedic sutures, orthopedic tapes, and orthopedic cords for attaching soft tissues to bone, a scaffold for repairing ligaments and tendons, and a scaffold for tissue engineering, ligaments, and tendons.

In another clinically significant aspect of this part of the present invention dealing with a fiber-reinforced composite comprising a matrix comprising a biodegradable, segmented, polyaxial copolyester and a reinforcement within the matrix, the reinforcement comprising a multifilament yarn of ultrahigh molecular weight polyethylene and at least one absorbable/biodegradable yarn comprising a heterochain polymer, the composite is in the form of (1) a tissue engineering scaffold for repairing or replacing maxillofacial tissues; (2) a surgical mesh for repairing or tissue engineering of soft tissues; or (3) a hernial repair mesh comprising a knitted construct as the fiber-reinforcing component. Furthermore, the present matrix may include at least one bioactive agent selected from antimicrobial agents, anti-inflammatory agents, antineoplastic agents, anesthetic agents, and tissue growth promoting agents.

For the second group, part of this inventions deals generally with a selectively absorbable/biodegradable, fibrous composite construct comprising less than about 70 percent by weight or less than 30 percent by weight of at least one biostable and one or more absorbable/biodegradable yarns assembled as initially interdependent, load-bearing components, transitioning to exhibit independent functional mechanical properties during in vivo end-use in degrading environments, wherein said fibrous composite construct is in the form of a composite warp-knitted mesh comprising at least one biostable and one or more absorbable/biodegradable yarns constructed as initially interdependent, interlacing, load-bearing components transitioning to exhibit independent functional properties during in vivo end-use in degrading environments, and wherein the biostable component comprises at least one multifilament or monofilament yarn made from polymers selected from the group consisting of ultrahigh molecular weight polyethylene (UHMW-PE), polypropylene, an aliphatic polyamide, an aromatic polyamide, polyether-ether ketone, and a polyalkylene terephthalate, while the absorbable/biodegradable component comprises at least one multifilament or monofilament yarn exhibiting enzymatic degradation, such as a silk and poly(3-hydroxyalkanoates) or hydrolytic degradation such as those comprising poly(2-hydroxyalkanoates). Furthermore, the biostable component comprises a multifilament yarn of ultrahigh molecular weight polyethylene and the absorbable/biodegradable component comprises at least one multifilament yarn of a thermoplastic polymer selected from the group consisting of segmented linear copolyesters, segmented polyaxial copolyesters, and copolymers of 3-hydroxybutyrate, and the absorbable/biodegradable component comprises a copolyester having repeat units derived from at least two cyclic monomers selected from the group consisting of glycolide, l-lactide, ε-caprolactone, and trimethylene carbonate.

Another aspect of this part of the invention deals with a selectively absorbable/biodegradable, fibrous composite construct comprising at least one biostable and one or more absorbable/biodegradable yarns assembled as initially interdependent, load-bearing components, transitioning to exhibit independent functional mechanical properties during in vivo end-use in degrading environments, wherein said fibrous composite construct is in the form of a composite warp-knitted mesh comprising at least one biostable and one or more absorbable/biodegradable yarns constructed as initially interdependent, interlacing, load-bearing components transitioning to exhibit independent functional properties during in vivo end-use in degrading environments, and wherein the mesh is coated with 0.1 to 10 percent of an absorbable polyaxial polyester and wherein the polyester is made of at least two cyclic monomers selected from the group consisting of glycolide, l-lactide, trimethylene carbonate, ϵ-caprolactone and a morpholinedione. Furthermore, the biostable component comprises at least one multifilament or monofilament yarn made from polymers selected from the group consisting of ultrahigh molecular weight polyethylene (UHMW-PE), polypropylene, an aliphatic polyamide, an aromatic polyamide, polyether-ether ketone, and a polyalkylene terephthalate, while the absorbable/biodegradable component comprises at least one multifilament or monofilament yarn exhibiting enzymatic degradation, such as a silk and poly(3-hydroxyalkanoates) or hydrolytic degradation such as those comprising poly(2-hydroxyalkanoates). Meanwhile, the biostable component comprises a multifilament yarn of ultrahigh molecular weight polyethylene and the absorbable/biodegradable component comprises at least one multifilament yarn of a thermoplastic polymer selected from the group consisting of segmented linear copolyesters, segmented polyaxial copolyesters, and copolymers of 3-hydroxybutyrate, and the absorbable/biodegradable component comprises a copolyester having repeat units derived from at least two cyclic monomers selected from the group consisting of glycolide, l-lactide, ϵ-caprolactone, and trimethylene carbonate.

A special aspect of this part of the invention deals with a selectively absorbable/biodegradable, fibrous composite construct comprising at least one biostable and one or more absorbable/biodegradable yarns assembled as initially interdependent, load-bearing components, transitioning to exhibit independent functional mechanical properties during in vivo end-use in degrading environments, wherein said fibrous composite construct is in the form of a composite warp-knitted mesh comprising at least one biostable and one or more absorbable/biodegradable yarns constructed as initially interdependent, interlacing, load-bearing components transitioning to exhibit independent functional properties during in vivo end-use in degrading environments. Meanwhile, the biostable component comprises polyethylene terephthalate multifilament yarn and the absorbable/biodegradable component comprises multifilament yarn of a linear or polyaxial segmented copolyester containing repeat units arising from at least two monomers selected from the group consisting of glycolide, l-lactide, ϵ-caprolactone, and trimethylene carbonate. Furthermore, the biostable component comprises polypropylene monofilament or multifilament yarn and the absorbable/biodegradable component comprises a multifilament yarn of a linear or polyaxial segmented copolyester containing repeat units arising from at least two monomers selected from the group consisting of glycolide, l-lactide, ϵ-caprolactone, and trimethylene carbonate.

Another special aspect of this part of the invention deals with a selectively absorbable/biodegradable, fibrous composite construct comprising at least one biostable and one or more absorbable/biodegradable yarns assembled as initially interdependent, load-bearing components, transitioning to exhibit independent functional mechanical properties during in vivo end-use in degrading environments, wherein said fibrous composite construct is in the form of a composite warp-knitted mesh comprising at least one biostable and one or more absorbable/biodegradable yarns constructed as initially interdependent, interlacing, load-bearing components transitioning to exhibit independent functional properties during in vivo end-use in degrading environments, and wherein the mesh is coated with 0.1 to 10 percent of an absorbable polyaxial polyester that is made of at least two cyclic monomers selected from the group consisting of glycolide, l-lactide, trimethylene carbonate, ϵ-caprolactone and a morpholinedione. Meanwhile, the biostable yarn component of the mesh comprises polyethylene terephthalate multifilament yarn and the absorbable/biodegradable yarn component comprises a multifilament yarn of a linear or polyaxial segmented copolyester containing repeat units arising from at least two monomers selected from the group consisting of glycolide, l-lactide, ϵ-caprolactone, and trimethylene carbonate. Furthermore, the biostable component comprises polypropylene monofilament or multifilament yarn and the absorbable/biodegradable component comprises a multifilament yarn of a linear or polyaxial segmented copolyester containing repeat units arising from at least two monomers selected from the group consisting of glycolide, l-lactide, ϵ-caprolactone, and trimethylene carbonate.

A clinically significant aspect of this part of the invention deals with a selectively absorbable/biodegradable, fibrous composite construct comprising at least one biostable and one or more absorbable/biodegradable yarns assembled as initially interdependent, load-bearing components, transitioning to exhibit independent functional mechanical properties during in vivo end-use in degrading environments, wherein said fibrous composite construct is in the form of a composite warp-knitted mesh comprising at least one biostable and one or more absorbable/biodegradable yarns constructed as initially interdependent, interlacing, load-bearing components transitioning to exhibit independent functional properties during in vivo end-use in degrading environments as, for instance, the use in hernial, vascular, and urological tissue repair and tissue engineering.

Another clinically significant aspect of this part of the invention deals with a selectively absorbable/biodegradable, fibrous composite construct comprising at least one biostable and one or more absorbable/biodegradable yarns assembled as initially interdependent, load-bearing components, transitioning to exhibit independent functional mechanical properties during in vivo end-use in degrading environments, wherein said fibrous composite construct is in the form of a composite warp-knitted mesh comprising at least one biostable and one or more absorbable/biodegradable yarns constructed as initially interdependent, interlacing, load-bearing components transitioning to exhibit independent functional properties during in vivo end-use in degrading environments, and wherein the mesh is coated with 0.1 to 10 percent of an absorbable polyaxial polyester, that is made of at least two cyclic monomers selected from the group consisting of glycolide, l-lactide, trimethylene carbonate, ϵ-caprolactone and a morpholinedione. Meanwhile, the said construct can be used in hernial, vascular, and urological tissue repair and tissue engineering. Additionally, the absorbable coating comprises one or more bioactive agent selected from the group known for their anti-inflammatory, anesthetic, antineoplastic, antimicrobial, microbicidal, antithrombic, and cell growth-promoting activities.

DETAILED DESCRIPTION OF PREFERRED EMBODIMENTS

This invention deals with a family of selectively absorbable/biodegradable, fibrous composite constructs comprising different combinations of biostable and absorbable/biodegradable yarns assembled as initially interdependent, load-bearing components, transitioning to exhibit independent functional properties during in vivo end-use. The family of constructs consists of two groups, one group is made of fiber-reinforced composites of high compliance, absorbable matrices of segmented polyaxial copolyesters reinforced with multifilament yarn constructs, which are combinations of ultrahigh molecular weight polyethylene fibers and at least one absorbable/biodegradable fiber selected from silk fibers and multifilament yarns made from linear segmented, l-lactide copolyesters and poly(3-hydroxyalkanoates), are useful in orthopedic, maxillofacial, urological, vascular, hernial repair and tissue engineering applications. The second group is made of coated and uncoated, warp-knitted mesh constructs for use in hernial, vascular, and urological tissue repair and tissue engineering. Meanwhile, both groups belonging to the family of selectively absorbable/biodegradable, fibrous, composite constructs comprising specially designed forms of warp-knitted mesh constructs. And these mesh constructs comprise combinations of absorbable/biodegradable and biostable yarns, which are different from all the mesh constructs of the prior art in being constructed from at least two types of yarns as initially interdependent, load-bearing components, transitioning to exhibit independent, functional properties during in vivo end use in biological tissues or under simulated in vitro degrading environments. More specifically, if for instance, one is dealing with two different yarns, namely an absorbable/biodegradable "A" and a biostable "B" in a warp-knitted construct, the strands of yarns A and B form two independent, interlacing networks at a predetermined number of junction points and, hence, provide initially shared load-bearing properties. Upon placing these constructs in a degrading environment, as in biological tissues, the absorbable/biodegradable strands "A" commence to gradually lose their strength and contribute less and less to the composite construct as load-bearing components. Eventually, the construct transitions the load-bearing function to the biostable yarn "B." For the first main type of warp-knitted mesh constructs, subject of this invention, the fibrous mesh construct is used to reinforce an absorbable, compliant matrix. On the other hand, the mesh constructs of the second main type can be coated with an absorbable, lubricious coating to mediate or prevent friction-induced abrasion and associated compromise of the mechanical properties due to the inherent, high modulus of any of the biostable component yarns. From a biomechanical perspective, an implant comprising the A and B components displays the high strength and modulus profiles required for providing the initial high load-bearing properties to maintain strong repaired tissue and then transitions gradually to a moderately strong and more compliant implant and transfers the load-bearing, incrementally, to the repaired tissue. This accelerates the tissue healing rate.

For the first main type of the family of constructs, part of the invention deals generally with a selectively absorbable/biodegradable, fiber-reinforced composite of a compliant absorbable, segmented polyaxial copolyester matrix reinforced with a multifilament yarn construct including a biostable yarn of ultrahigh molecular weight polyethylene and at least one absorbable/biodegradable yarn of heterochain, natural, biosynthetic, or synthetic polymer. Differences between the fiber-reinforced composites, subject of this part of the invention, and those of the relevant prior art, which in part, led to the pursuit of the study of this part of the invention, are outlined in the paragraphs below.

Traditionally, the fibrous components in fiber-reinforced composites of thermoplastics or thermosets constitute about 10 percent to about 90 percent of their total mass and are designed to be responsible for increasing the modulus, and in most cases, the mechanical strength of their respective matrices. Conversely, this invention deals with unconventional, new forms of fiber-reinforced composites where the matrices are designed to mediate the extreme physicochemical properties of high modulus, reinforcing fibrous components to improve their mechanical biocompatibility and subsequently, allow their beneficial uses in clinically significant biomedical applications. Specifically, the present invention is directed to composites of ultrahigh molecular weight polyethylene (UHMW-PE) fibers having exceptionally high tensile strength and modulus as one of the fibrous reinforcing components of low-modulus, highly complaint polymeric matrices which are designed to mediate the engineering stiffness of UHMW-PE fibers when used in implantable devices or parts thereof. Accordingly, the biological tissues surrounding an implanted composite device will be directly interfacing with a highly compliant matrix, and not the high-modulus, reinforcing fibers, which minimizes or eliminates potential mechanical damage to the cellular components of biological tissues.

With a few exceptions, the traditional implantable, fiber-reinforced composite devices are either totally absorbable or non-absorbable. The non-absorbable types of fiber-reinforced composites are expected to be functionally load-bearing for prolonged use, which can occasionally be associated with increased incidences of infection at the implantation sites. On the other hand, the absorbable types of fiber-reinforced composites are designed to be transient in nature, thus allowing a gradual transfer of the mechanical function to the natural tissues and finally absorb, thereby minimizing the likelihood of infection due to the residing mass of the device. However, when absorbable composites are used as load-bearing devices, the mechanical strength retention decreases with time, which can occasionally be associated with premature loss of mechanical integrity due to unforeseen biological factors, thereby leading to failure in their functional mechanical performance. This led to the contemporary use of blends of absorbable and non-absorbable fibers in order to combine the advantages of the absorbable fibers and their eventual mass loss with those of non-absorbable fibers exhibiting prolonged retention of their mechanical properties. However, when non-absorbable fibers are made of the high modulus UHMW-PE, mere blending with polydioxanone (PDS) fibers does not mediate the direct interfacing of biological tissues to prevent the mechanical damage of those stiff fibers to the cellular components of these tissues. Accordingly, this part of the invention provides unique combinations of ultrahigh strength, non-absorbable fibers such as those of UHMW-PE and absorbable/biodegradable fibers as reinforcing components of low modulus, high compliance absorbable matrices for effective use in load-bearing devices with modulated, time-dependent properties. In effect, the composites, subject of this part of the invention, are designed to (1) provide an exceptional load-bearing strength in the initial period of clinical use while presenting the biological tissue with a compliant surface for optimum interfacing with mechanically sensitive cellular components; (2) produce biomechanically effective implants with minimum volume for a timely displacement by natural tissue—this is to maximize the mechanical biocompatibility and minimize patient discomfort; (3) exhibit gradual tensile loss due to the absorption of the absorbable fiber components and hence, allowing load transfer to the natural tissue, which in turn accelerates tissue healing and regain of natural tissue strength; and (4) provide prolonged maintenance of critical load-bearing properties, which are far less than those initially needed, with minimum fiber mass due to the contribution of the exceptionally strong UHMW-PE fibers. In spite of the claimed advantage of the UHMW-PE/PDS fiber combination over a totally non-absorbable combination of UHMW-PE and polyethylene terephthalate fibers in commercially available orthopedic sutures and allied products, the breaking strength retention profile of PDS is too short for the effective use in low-healing orthopedic tissues. Accordingly, this part of the invention deals with the use of fiber combinations featuring UHMW-PE as the non-absorbable component and slow-absorbing fibers, such as those based on high-lactide, segmented copolyesters, poly(3-hydroxyalkanoates), and silk as the absorbable/biodegradable components in conjunction with the added feature of being the reinforcing elements in an absorbable, compliant matrix. For fine tuning or optimizing the performance of the fiber-reinforced composites subject of this invention, the UHMW-PE fibers can be used with one or more of the absorbable fibers to achieve the unique feature of modulated strength retention and mass loss profiles that are controlled by (1) the hydrolytic degradation of the lactide copolymer; (2) the enzymatic degradation of silk or poly(3-hydroxyalkanoates); or (3) combination of hydrolytic and enzymatic degradation.

When the composites, subject of this part of the invention, are intended for use as knotted anchoring suture devices, in another aspect of this invention it is recognized that the stabilization of the suture knots is achieved through the use of the absorbable cyanoacrylate tissue adhesive formulation disclosed by one of the present inventors (U.S. Pat. No. 6,723,114, hereby incorporated herein by reference) as a knot stabilizer, which increases the knot security. Another aspect of this invention deals with the use of fiber-reinforced composites disclosed herein as surgical meshes and particularly those used for hernial tissue repair.

A clinically interesting feature of the selectively absorbable/biodegradable, fiber-reinforced composite subject of this part of the invention is the ability to incorporate one or more bioactive agent(s) in the polyaxial matrix. Among these agents are those known to exhibit antimicrobial activity, anti-inflammatory, anesthetic, antineoplastic and tissue growth promoting activities.

For the second main type of the family of selectively absorbable/biodegradable, fibrous, composite constructs, part of this invention deals generally with selectively absorbable/biodegradable, composite, warp-knitted mesh comprising at least one biostable and one or more absorbable/biodegradable yarns constructed initially as interdependent, interlacing, load-bearing components transitioning to exhibit independent functional mechanical properties during in vivo end-use as in the biological tissues or simulated in vitro environments. The rationale for using such warp-knitting design for changing the role of the yarn components gradually during end-use is the same as the one cited above upon discussing the first main type of the family of constructs dealing with the fiber-reinforced, compliant absorbable matrix. However, the constructs of the second group are distinguished for being simply fibrous composites, which may be coated with a lubricious absorbable coating to impart desirable frictional properties as well as providing, incrementally, additional space for allowing timely tissue ingrowth into the mesh as the coating loses its mass and physical presence as a result of absorption caused by hydrolytic degradation. The use of the lubricious coating is more significant in composite constructs comprising inherently rigid, high modulus yarns such as those of ultrahigh molecular weight polyethylene, polyether-ether ketone, highly oriented polyester or polypropylene yarns. This is because the coating is designed to mediate the friction-induced mechanical damage affecting the mechanically heterogeneous composite constructs during and after implementation. Furthermore, as the coating absorbs and undergoes incremental loss of mass and physical presence, it permits gradual tissue ingrowth at healing biological tissues. This, in turn, results in mechanical stabilization of the construct as a surgical mesh and vascular graft or patch.

Further illustrations of the present invention are provided by the following examples:

EXAMPLE 1

General Method for Synthesis and Characterization of Absorbable, Segmented, Polyaxial Copolyesters as Compliant Coating and Matrix Materials The synthesis of these copolyesters entails the two general steps described in U.S. Pat. Nos. 6,462,169 and 6,794,364, both of which are hereby incorporated herein by reference. The first step deals with the synthesis of an amorphous, polyaxial, polymeric initiator; typically, the polymerization of a mixture of ϵ-caprolactone, glycolide, and/or trimethylene carbonate in the presence of triethanolamine or trimethylolpropane as the initiator and stannous octanoate as the catalyst. The copolymerization was conducted under a dry nitrogen atmosphere while stirring the reaction mixture in a predried reactor at 160-170° C. until practically complete monomer conversion was achieved as determined by gel-permeation chromatography (GPC). Samples of the resulting amorphous polymeric initiator were characterized for molecular weight by GPC. The second step consists of end-grafting the polymeric initiator from step one with a mixture of ϵ-caprolactone and glycolide or l-lactide. Depending on the composition of the end-grafted monomeric mixture, an additional amount of the catalyst was added. The end-grafting was conducted under a dry nitrogen atmosphere at about 160° C. until practically a complete conversion of the monomers was achieved. The resulting copolyester was purified, first by heating under reduced pressure at 80° C. to remove most of the residual monomers. Further purification was then pursued by dissolving the polymer in acetone and precipitation in cold 2-propanol. The precipitated polymer was isolated and dried at ambient temperature and pressure and then under reduced pressure until a constant weight was attained. The purified copolyester was characterized for molecular weight and purity by GPC, thermal properties, namely melting temperature ($T_m$) and heat of fusion ($\Delta H_f$) by differential scanning calorimetry (DSC), and identify by IR and NMR.

EXAMPLE 2

Synthesis and Characterization of Two Typical Absorbable Polyaxial Copolyesters as Matrix Materials (PX-1 to PX-3)

The three copolymers were prepared and characterized following the general scheme described in Example 1. The specific polymerization conditions and analytical data are summarized in Table I.

TABLE I

Polymerization Scheme and Analytical Data for PX-1 to PX-3

| Polymerization Scheme and Analytical Data | PX-1 | PX-2 | PX-3 |
|---|---|---|---|
| Polymeric Initiator: | | | |
| Monomers, type[a], molar ratio | CL/TMC, 90/10 | CL/TMC, 90/10 | CL/TMC/G 35/14/9 |
| Trifunctional initiator: | | | |
| Type[b] | TMP | TEA | TEA |
| Monomer/Initiator (molar) | 8/1 | 20/1 | 460/1 |
| Stannous Octanoate, Monomer/Catalyst (molar) | 2,000 | 2,000 | 32,000 |
| Reaction Temperature: | 160° C. | 160° C. | 180° C. |
| Mol. Wt. (GPC) $M_n$, $M_w$ (kDa) | 1.6, 2.7 | 4.9, 15 | 60, 100 |
| Crystalline Copolyester: | | | |
| Polymeric Initiator/Monomers weight ratio | 10/90 | 15/85 | 53/47 |
| Monomers, type[a], molar ratio | CL/G, 95/5 | CL/G, 95/5 | L/G 34/8 |
| Stannous Octanoate, Monomer/Catalyst (molar ratio) | 10,000 | 10,000 | 12,000 |
| Reaction Temperature | 160° C. | 160° C. | 140° C. |
| Analytical Data: | | | |
| GPC: $M_n$, $M_w$ (kDa) | 18, 51 | 27, 92 | 90, 150 |
| DSC: $T_m$, ° C. | 43 | 46 | 105 |
| ΔH, J/g | 48 | 51 | 7.2 |

[a]CL = ε-caprolactone; TMC = trimethylene carbonate; G = glycolide; L = l-lactide.
[b]TEA = triethanolamine, TMP = trimethylolpropane.

EXAMPLE 3

Preparation of Typical High Glycolide and l-Lactide Segmented Polyesters (SGs and SLs)

Two high glycolide-based copolymers, SG-1 and SG-2, and two high lactide-base copolymers, SL-1 and SL-2, were prepared as outlined below:

Preparation of SG-1: A 95/5 (molar) mixture of glycolide/l-lactide was polymerized under traditional ring-opening polymerization using stannous octanoate as a catalyst and 1-decanol as the initiator at a maximum polymerization temperature of 220° C. until practically complete conversion was achieved. The polymer was isolated, ground, dried, and residual monomers were removed by distillation under reduced pressure. The purified polymer was characterized for identity and composition (IR and NMR), thermal properties (DSC), and molar weight (inherent viscosity in hexafluoroisopropyl alcohol, HFIP).

Preparation of SG-2: A mixture of 95/5 (molar) glycolide/ε-caprolactone was end-grafted onto polyaxial polytrimethylene carbonate as a polymeric initiator to produce SG-2, using similar conditions to those disclosed in U.S. Pat. Nos. 6,498,229 and 6,462,169, each hereby incorporated herein by reference, for preparing the polymeric polyaxial initiator and completing the end-grafting scheme, respectively. The polymer was isolated, ground, dried, purified, and characterized as described for SG-1.

Preparation of SL-1: The copolymer was prepared using 88/12 (molar) l-lactide/trimethylene carbonate as per the teaching of U.S. Pat. No. 6,342,065, hereby incorporated herein by reference. The polymer was isolated, ground, dried, purified, and characterized as described for SG-1 above with the exception of using chloroform as a solvent for the solution viscosity measurement.

Preparation of SL-2: The copolymer was prepared using 84/11/5 (molar) l-lactide/trimethylene carbonate/caprolactone as per the teaching of U.S. Pat. No. 6,342,065. The polymer was isolated, ground, dried, purified, and characterized as described for SL-1.

EXAMPLE 4

General Method for Preparation of Multifilament Yarns

Copolyesters GS-1, GS-2, SL-1 and SL-2 from Example 3 were melt-spun using a ¾" extruder equipped with a 10- or 20-hole die following the general protocol described in U.S. Pat. No. 6,342,065. The extruded yarns were oriented during a two-stage drawing using a series of heated Godets.

EXAMPLE 5

General Method of Composite Assembling

A braid construct comprising UHMW-PE multifilament yarn and one or two absorbable biodegradable multifilament yarn(s) was prepared. The braid was then impregnated with the polyaxial matrix polymer according to the following steps:

(1) Threading the braid through a 10 to 30 percent solution of the matrix polymer in acetone or a mixture of chloroform and dichloromethane while being under tension;

(2) Passing the impregnated braid through a heated forced air oven (40-50° C.) for removing most of the solvent;

(3) Sintering the matrix about the braided multifilaments by passing through a heated air oven while applying sufficient tension to achieve up to 5 percent increase in length at the prevailing sintering temperatures; and (4) Spooling the sintered composites and drying at ambient pressure and temperature and then under reduced pressure.

EXAMPLE 6

General Method for Determination of the Weight Percentage of the Composite Constituents The weight percent of the matrix in the composite was determined through determining the dry add-on of the matrix polymer to the braided construct. Alternatively, the matrix polymer was extracted from the composite to determine the add-on. The initial weight percentages of the UHMW-PE and the absorbable/biodegradable components in the braided construct can be calculated from the total yarn denier of the individual components used to produce the braid. For determining the final weight percent of UHMW-PE in the braided construct: (1) a known weight of the braided construct was digested in a KOH solution in aqueous methanol at 50° C. to degrade the absorbable/biodegradable components of the composite; (2) the remaining mass was rinsed with deionized water to isolate the intact UHMW-PE, which was then dried to a constant weight; and (3) the dry weight of the remaining UHMW-PE was used to determine its percentage in the original braided construct. For biodegradable components comprising a mixture of silk and high-lactide copolymer, the braid was first extracted with chloroform to remove the latter and then digested in a KOH solution to remove the silk and determine their individual weight percents.

EXAMPLE 7

General Method for Evaluation of the Composite In Vitro Properties

For physicomechanical properties, the composites were evaluated using an MTS Synergie Model 200 Tester for linear breaking load, knot breaking load, and percentage elongation.

To determine the in vitro linear breaking load retention (BLR), after incubating in a degrading medium: (1) a phosphate buffer at pH 7.4 and 37° C. or 50° C. was used to assess the effect of hydrolytic degradation on percent BLR absorbable components of the composite; and (2) a solution of a suitable enzyme (e.g., a protease for silk and esterase for polyesters) at pH 7.2 and 37° C. was used to determine the combined effect of hydrolytic, but primarily, enzymatic degradation on the composite BLR.

EXAMPLE 8

Preparation and Testing of a Typical Composite of Polyaxial Polyester Reinforced with Braided Multifilaments of UHMW-PE and Segmented l-Lactide Copolymer Three-ply UHMW-PE multifilament yarn (120 ends, 667 denier) and multifilament yarn (43 ends, 80 denier) of segmented l-lactide copolymer made earlier in this laboratory, as described in U.S. Pat. No. 6,342,065, from about an 88/12 l-lactide/trimethylene carbonate were used in preparing the braided multifilament construct. The latter was made on a 12-carrier braider using the UHMW-PE as the core and the l-lactide copolymer as the sheath. The braided construct was then impregnated with a 16 percent acetone solution of the polyaxial matrix polymer, PX-3 (from Example 2). The impregnated construct was sintered at 80° C. under needed tension to achieve an initial increase in unit length of about 5 percent.

The braids and sintered composite were tested as in Examples 4 and 5 to obtain the following results:
Braided Multifilament—UHMW-PE in braid=73% by weight; l-lactide polyester in braid=27%.
Composite—Matrix/Braid (weight ratio)=12/88; Diameter=0.69 mm; Linear Breaking Load=94 lb.; Elongation=55%; Knot Breaking Load=58 lb.

EXAMPLE 9

Preparation and Testing of a Typical Composite of Polyaxial Polyester Reinforced with Braided Multifilament of UHMW-PE and Degummed Silk The composite was prepared as described in Example 6 with the exception of using (1) a three-ply construct of a silk multifilament yarn (15 ends, 20 denier) instead of the l-lactide copolymeric multifilaments; (2) a sintering temperature of 70° C.; and (3) a tension during sintering to achieve an initial increase in unit length of about 3 percent.

The braids and sintered composite were tested as described in Examples 4 and 5 to obtain the following results:
Braided Multifilament—UHMW-PE in the braid=70%; Silk in the braid=30%.
Composite—Matrix/Braid (weight ratio)=11/89; Diameter=0.68 mm; Linear Breaking Load=114 lb; Elongation=38%; Knot Breaking Load=57 lb.

EXAMPLE 10

Preparation and Testing of a Typical, Selectively Absorbable, Warp-Knitted Mesh (WKM-1) Using Multifilament Yarns of UHMW-PE Plying and Characteristics of Yarn Preparation
1. Yarn A (1-ply natural yarn of UHMW-PE)
   Twist Count: 140 t/m S
   Denier Range: 50-60 g/9000 m
   Tenacity Range: 30-40 g/denier
   Ultimate Elongation: 3-5%
2. Yarn B (1-ply natural yarn of segmented polyaxial copolyester SG-2 from Example #3)
   Fiber Count: 10
   Denier Range: 120-170 g/9000 m
   Tenacity Range: 3.5-5.5 g/denier
   Ultimate Elongation: 40-70%
General Method for Composite Mesh Construction—Composition consisting of yarns A and B of which yarn A is biostable and yarn B is biodegradable. Each pattern was knitted using a composite construction made from two individual patterns that coexist in one mesh. Knit constructions were produced using a two-step process of warping yarn onto beams and constructing meshes using a raschel or tricot knitting machine of the standard art. Knit constructions can be made from multifilament yarn, monofilament yarn, or combinations therefrom. Knit mesh was heat set or annealed at 120° C. for 1 hour while under strain in the wale and course directions.

Knitting Process of Mesh Pattern—The knitting process utilized two warped beams of yarn A threaded on bars 1 and 2 and two warped beams of yarn B threaded on bars 3 and 4. The knitting machine was a Raschel knitting machine of 18 gauge needles. Yarn B was knitted in a 2 bar marquisette pattern and yarn A knitted in a 2 bar sand-fly net pattern with all guide bars for each pattern threaded 1-in and 1-out.
Knitting Pattern (28 Courses Per Inch)
Bar 1—1-0/1-2/2-3/2-1//2× (1-in, 1-out)
Bar 2—2-3/2-1/1-0/1-2//2× (1-in, 1-out)
Bar 3—1-0/0-1//4× (1-in, 1-out)
Bar 4—0-0/3-3//4× (1-in, 1-out)
Characterization and In Vitro Evaluation of Typical Composite Meshes—In vitro conditioned burst strength retention [BSR=(max. load at time point/initial max. load)×100] was conducted using a MTS MiniBionix Universal Tester (model 858) equipped with a burst test apparatus as detailed in ASTM D3787-01. Samples were tested initially and after in accelerated in vitro conditioning using a 0.1M solution of buffered sodium phosphate at 12.0 pH and at a temperature of 50° C. for 5 days. Samples incubated at 50° C. were placed in 50 mL tubes and under constant orbital-agitation. Samples were removed at the predetermined time point for mechanical and physical properties testing (n=4).

Warp Knit Composite Mesh Physical Properties

TABLE II

Warp Knit Composite Mesh Tabulated Physical Properties

| Knitting Pattern | Area Weight ($g/m^2$) | Yarn B Content (weight %) |
|---|---|---|
| WKM-1 | 79 | 67 |

Resultant Mesh Mechanical Properties

TABLE III

Warp Knit Composite Mesh Initial Burst Properties Reported with Standard Deviations (n = 4)

| Sample Description | Max. Burst Force (N) | | Elongation at Maximum Force (mm) | | Elongation at 71 N Force (mm) | | Elongation at 16 N/cm (%) |
|---|---|---|---|---|---|---|---|
| WKM-1 | 401 | ±43 | 15.26 | ±0.44 | 8.15 | ±0.2 | 7.5 |

TABLE IV

Warp Knit Composite Mesh Following Accelerated In Vitro Conditioning (12 pH, 50° C., 5 days) Reported with Standard Deviations (n = 3)

| Sample Description | Max. Burst Force (N) | | Elongation at Maximum Force (mm) | | Elongation at 71 N Force (mm) | | Elongation at 16 N/cm (%) |
|---|---|---|---|---|---|---|---|
| WKM-1 | 400 | ±7 | 22.05 | ±.70 | 18.49 | ±1.17 | 33.9 |

EXAMPLE 11

Surface Coating of a Warp-knitted Mesh (WKM-1) with PX-2 (from Example #2) and Testing of Coated Mesh (WKM-1C)

General Method for Mesh Coating—Impregnating polymers or coatings can be applied following annealing to modify in vivo and/or in vitro characteristics. Meshes were coated using an 8 g/100 mL solution of PX-2 polymer and acetone solvent, respectively. The coating was applied using a solution casting method where each mesh was submerged in the solution, removed, blotted to remove excess solution, and then dried to a constant weight.

Characterization and In Vitro Evaluation of Typical Composite Meshes—In vitro conditioned burst strength retention [BSR=(max. load at time point/initial max. load)×100] was conducted using a MTS MiniBionix Universal Tester (model 858) equipped with a burst test apparatus as detailed in ASTM D3787-01. Samples were tested for their physical and mechanical properties testing (n=4).

Coated Warp Knit Composite Mesh (WKM-1C) Physical Properties

TABLE V

Warp Knit Composite Mesh Tabulated Physical Properties

| Knitting Pattern | Area Weight ($g/m^2$) | Coating Add-on (weight %) |
|---|---|---|
| WKM-1C | 83 | 5 |

Resultant Mechanical Properties of Resultant Coated Mesh, WKM-1C

TABLE VI

PX-2 Coated Warp Knit Composite Mesh Initial Burst Properties Reported with Standard Deviations (n = 4)

| Sample Description | Max. Burst Force (N) | | Elongation at Maximum Force (mm) | | Elongation at 71 N Force (mm) | | Elongation at 16 N/cm (%) |
|---|---|---|---|---|---|---|---|
| WKM-1C | 422 | ±27 | 14.75 | ±0.71 | 7.22 | ±0.99 | 5.9 |

EXAMPLE 12

Impregnation of a Warp-Knitted Mesh (WKM-1) with PX-3 Matrix Polymer (from Example #2) and Testing of the Composite Mesh (WKM-1M)

General Method for Mesh Impregnation—Impregnation with matrix polymer can be applied following annealing to modify in vivo and/or in vitro characteristics. WKM-1 meshes were impregnated with a matrix polymer using a 26 g/100 mL solution of PX-3 polymer in acetone. The matrix polymer was applied using a solution casting method where each mesh was submerged in the solution, removed, blotted to remove excess solution, and then dried to a constant weight.

Characterization and In Vitro Evaluation of Typical Composite Meshes—In vitro conditioned burst strength retention [BSR=(max. load at time point/initial max. load)×100] was conducted using a MTS MiniBionix Universal Tester (model 858) equipped with a burst test apparatus as detailed in ASTM D3787-01. Samples were tested for their physical and mechanical properties testing (n=4).

Impregnated Warp Knit Composite Mesh (WKM-1M) Physical Properties

TABLE VII

Warp Knit Composite Mesh Tabulated Physical Properties

| Knitting Pattern | Area Weight ($g/m^2$) | Matrix Polymer (Weight %) |
|---|---|---|
| WKM-1M | 111 | 40 |

Resultant Mechanical Properties of Resultant Impregnated Mesh, WKM-1M

TABLE VIII

PX-2 Impregnated Warp Knit Composite Mesh (WKM-1M) Initial Burst Properties Reported with Standard Deviations (n = 4)

| Sample Description | Max. Burst Force (N) | | Elongation at Maximum Force (mm) | | Elongation at 71 N Force (mm) | | Elongation at 16 N/cm (%) |
|---|---|---|---|---|---|---|---|
| WKM-1M | 425 | ±23 | 14.13 | ±0.96 | 7.12 | ±0.71 | 5.7 |

EXAMPLE 13

Preparation and Testing of a Typical, Selectively Absorbable, Warp-Knitted Mesh (WKM-2) Using Multifilament Yarns of Polyethylene Terephthalate (PET)

Plying and Characteristics of Yarn Preparation
1. Yarn A (2-ply natural PET yarn)
   Denier Range: 90-110 g/9000 m
   Tenacity Range: 3-6 g/denier
2. Yarn B (1-ply natural yarn of segmented polyaxial copolyester SG-2 from Example #3)
   Fiber Count: 10
   Denier Range: 120-170 g/9000 m
   Tenacity Range: 3.5-5.5 g/denier
   Ultimate Elongation: 40-70%

General Method for Composite Mesh Construction—Composition consisting of yarns A and B of which yarn A is biostable and yarn B is biodegradable. Each pattern was knitted using a composite construction made from two individual patterns that coexist in one mesh. Knit constructions were produced using a two step process of warping yarn onto beams and constructing meshes using a raschel or tricot knitting machine of the standard art. Knit constructions can be made from multifilament yarn, monofilament yarn, or combinations therefrom. Knit mesh was heat set or annealed at 120° C. for 1 hour while under strain in the wale and course directions.

Knitting Process of Mesh Pattern—The knitting process utilized two warped beams of yarn A threaded on bars 1 and 2 and two warped beams of yarn B threaded on bars 3 and 4. The knitting machine was a Raschel knitting machine of 18 gauge needles. Yarn B was knitted in a 2 bar marquisette pattern and yarn A knitted in a 2 bar sand-fly net pattern with all guide bars for each pattern threaded 1-in and 1-out.

Knitting Pattern (28 Courses Per Inch)
Bar 1—1-0/1-2/2-3/2-1//2× (1-in, 1-out)
Bar 2—2-3/2-1/1-0/1-2//2× (1-in, 1-out)
Bar 3—1-0/0-1//4× (1-in, 1-out)
Bar 4—0-0/3-3//4× (1-in, 1-out)

Characterization and In Vitro Evaluation of Typical Composite Meshes—In vitro conditioned burst strength retention [BSR=(max. load at time point/initial max. load)×100] was conducted using a MTS MiniBionix Universal Tester (model 858) equipped with a burst test apparatus as detailed in ASTM D3787-01. Samples were tested initially and after in accelerated in vitro conditioning using a 0.1M solution of buffered sodium phosphate at 12.0 pH and at a temperature of 50° C. for 5 days. Samples incubated at 50° C. were placed in 50 mL tubes and under constant orbital-agitation. Samples were removed at the predetermined time point for mechanical and physical properties testing (n=4).

Warp Knit Composite Mesh Physical Properties

TABLE IX

Warp Knit Composite Mesh Tabulated Physical Properties

| Knitting Pattern | Area Weight (g/m$^2$) | Yarn B Content (weight %) |
|---|---|---|
| WKM-2 | 167 | 33 |

Resultant Mesh Mechanical Properties

TABLE X

Warp Knit Composite Mesh Initial Burst Properties Reported with Standard Deviations (n = 4)

| Sample Description | Maximum Burst Force (N) | | Elongation at Maximum Force (mm) | | Elongation at 71 N Force (mm) | | Elongation at 16 N/cm (%) |
|---|---|---|---|---|---|---|---|
| WKM-2 | 506 | ±20 | 18.41 | ±0.73 | 8.81 | ±0.57 | 8.8 |

TABLE XI

Warp Knit Composite Mesh Following Accelerated In Vitro Conditioning (12 pH, 50° C., 5 days) Reported with Standard Deviations (n = 4)

| Sample Description | Maximum Burst Force (N) | | Elongation at Maximum Force (mm) | | Elongation at 71 N Force (mm) | | Elongation at 16 N/cm (%) |
|---|---|---|---|---|---|---|---|
| WKM-2 | 366 | ±14 | 25.08 | ±0.92 | 18.15 | ±0.64 | 32.8 |

EXAMPLE 14

Surface Coating of a Warp-knitted Mesh (WKM-2) with PX-2 (from Example #2) and Testing of Coated Mesh (WKM-2C)

General Method for Mesh Coating—Coating can be applied following annealing to modify in vivo and/or in vitro characteristics. Meshes were coated using an 8 g/100 mL solution of PX-2 polymer and acetone solvent, respectively. The coating was applied using a solution casting method where each mesh was submerged in the solution, removed, blotted to remove excess solution, and then dried to a constant weight.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. Thee subranges are also useful in carrying out the present invention.

What is claimed is:

1. An absorbable/biodegradable implant, fibrous composite construct comprising a fiber-reinforced matrix, the fiber-reinforced matrix comprising a biodegradable, segmented, polyaxial copolyester, the fiber-reinforced matrix comprising from about 10 percent to about 40 percent by weight of the absorbable/biodegradable implant, fibrous composite construct, the fiber-reinforced matrix further comprising
    i) a reinforcement comprising less than 40 percent by weight of at least one biostable yarn comprising a multifilament yarn of ultrahigh molecular weight polyethylene, wherein the biostable yarn of the reinforcement is surrounded by the fiber-reinforced matrix,
    ii) and at least one absorbable/biodegradable yarn comprising a heterochain polymer,
    wherein the at least one biostable yarn and the at least one absorbable/biodegradable yarn assembled as initially interdependent, load-bearing components, and
    wherein the biostable and biodegradable yarns transition during in vivo end-use to exhibit independent functional mechanical properties.

2. The absorbable/biodegradable, fibrous composite construct as in claim 1 wherein the biodegradable, segmented polyaxial copolyester of the matrix comprises an amorphous, polyaxial, polymeric initiator end-grafted with a mixture of ε-caprolactone and at least one cyclic monomer selected from the group consisting of l-lactide, dl-lactide, glycolide, and trimethylene carbonate, such that crystallizable terminal segments are formed.

3. The absorbable/biodegradable, fibrous composite construct as in claim 2 wherein the amorphous, polyaxial, polymeric initiator is formed by the ring-opening polymerization of trimethylene carbonate in the presence of a catalyst comprising stannous octanoate and a monocentric polyfunctional initiator selected from the group consisting of triethanolamine, trimethylolpropane, and pentaerythritol.

4. The absorbable/biodegradable, fibrous composite construct as in claim 2 wherein the amorphous, polymeric initiator is formed by the ring-opening polymerization of a mixture of trimethylene carbonate and at least one monomer selected from the group consisting of p-dioxanone, ε-caprolactone, and 1,5-dioxepan-2-one.

5. The absorbable/biodegradable, fibrous composite construct as in claim 1 wherein the biodegradable yarn comprises at least one polymer selected from the group consisting of silk protein, a linear, segmented l-lactide copolyester, and a poly(3-hydroxyalkanoate).

6. The absorbable/biodegrable, fibrous composite construct as in claim 5 wherein the biodegradable yarn comprises silk protein in the form of degummed, white Brazilian raw *Bombyx mori* silkworm fibers.

7. The absorbable/biodegradable, fibrous composite construct as in claim 5 wherein the biodegradable yarn comprises a segmented copolymer of l-lactide and at least one monomer selected from the group consisting of glycolide, ε-caprolactone, trimethylene carbonate, p-dioxanone, and a morpholinedione.

8. The absorbable/biodegradable, fibrous composite construct as in claim 5 wherein the biodegradable yarn comprises a poly(3-hydroxyalkanoate) selected from the group consisting of poly(3-hydroxybutyrate) and poly(3-hydroxybutyrate-co-3-hydroxyvalerate).

9. The absorbable/biodegradable, fibrous composite construct as in claim 1 in the form of an orthopedic device.

10. The absorbable/biodegradable, fibrous composite construct as in claim 9 wherein the orthopedic device is selected from the group consisting of orthopedic sutures, orthopedic tapes, and orthopedic cords for attaching soft tissues to bone.

11. The absorbable/biodegradable, fibrous composite construct as in claim 9 wherein the orthopedic device is a scaffold for repairing ligaments and tendons.

12. The absorbable/biodegradable, fibrous composite construct as in claim 9 wherein the orthopedic device is a scaffold for tissue engineering ligaments, and tendons.

13. The absorbable/biodegradable, fibrous composite construct as in claim 1 the form of a tissue engineering scaffold for repairing or replacing maxillofacial tissues.

14. The absorbable/biodegradable, fibrous composite construct as in claim 1 in the form of a surgical mesh for repairing or tissue engineering of soft tissues.

15. The absorbable/biodegradable, fibrous composite construct as in claim 1 in the form of a hernial repair mesh and wherein the fibrous construct comprises a knitted construct.

16. The absorbable/biodegradable, fibrous composite construct as in claim 1 wherein the matrix further comprises at least one bioactive agent selected from the group consisting of agents, and tissue growth promoting agents.

17. The absorbable/biodegradable, fibrous composite construct as in claim 1 wherein the at least one biostable yarn comprises less than about 30 percent by weight of the construct.

18. The absorbable/biodegradable implant, fibrous composite construct as in claim 1 in the form of a warp-knitted mesh wherein the warp-knitted mesh is coated with 0.1 to 10 percent of an absorbable polyaxial polyester and wherein the polyester is made of at least two cyclic monomers selected from the group consisting of glycolide, l-lactide, trimethylene carbonate, ε-caprolactone and a morpholinedione.

19. The absorbable/biodegradable, fibrous composite construct as in claim 1 wherein the biostable yarn comprises at least one additional multifilament or monofilament yarn made from polymers selected from the group consisting of ultrahigh molecular weight polyethylene (UHMW-PE), polypropylene, an aliphatic polyamide, an aromatic polyamide, polyether-ether ketone, and a polyalkylene terephthalate, and wherein the absorbable/biodegradable yarn comprises at least one multifilament or monofilament yarn selected from the group consisting of silk, poly(3-hydroxyalkanoates), and poly(2-hydroxyalkanoates).

20. The absorbable/biodegradable, fibrous composite construct as in claim 18 wherein the biostable yarn comprises at least one additional multifilament or monofilament yarn made from polymers selected from the group consisting of ultrahigh molecular weight polyethylene (UHMW-PE), polypropylene, an aliphatic polyamide, an aromatic polyamide, polyether-ether ketone, and a polyalkylene terephthalate, and wherein the absorbable/biodegradable yarn comprises at least one multifilament or monofilament yarn selected from the group consisting of silk, poly(3-hydroxyalkanoates), and poly(2-hydroxyalkanoates).

21. The absorbable/biodegradable, fibrous composite construct as in claim 19 wherein the biostable yarn comprises a multifilament yarn of ultrahigh molecular weight polyethylene and the absorbable/biodegradable yarn comprises at least one multifilament yarn of a thermoplastic polymer selected from the group consisting of segmented linear copolyesters, segmented polyaxial copolyesters, and copolymers of 3-hydroxybutyrate.

22. The absorbable/biodegradable, fibrous composite construct as in claim 21 wherein the absorbable/biodegradable yarn comprises a copolyester having repeat units derived from at least two cyclic monomers selected from the group consisting of glycolide, l-lactide, ε-caprolactone, and trimethylene carbonate.

23. The absorbable/biodegradable, fibrous composite construct as in claim 20 wherein the biostable yarn comprises a multifilament yarn of ultrahigh molecular weight polyethylene and the absorbable/biodegradable yarn comprises at least one multifilament yarn of a thermoplastic polymer selected from the group consisting of segmented linear copolyesters, segmented polyaxial copolyesters, and copolymers of 3-hydroxybutyrate.

24. The absorbable/biodegradable, fibrous composite construct as in claim 20 wherein the absorbable/biodegradable yarn comprises a copolyester having repeat units derived from at least two cyclic monomers selected from the group consisting of glycolide, l-lactide, ε-caprolactone, and trimethylene carbonate.

25. The absorbable/biodegradable, fibrous composite construct as in claim 1 further comprising an additional biostable yarn comprising a polyethylene terephthalate multifilament yarn and the absorbable/biodegradable yarn comprises a multifilament yarn of a linear or polyaxial segmented copolyester containing repeat units derived from at least two monomers selected from the group consisting of glycolide, l-lactide, ε-caprolactone, and trimethylene carbonate.

26. The absorbable/biodegradable, fibrous composite construct as in claim 1 further comprising an additional biostable yarn comprising a polypropylene monofilament or multifilament yarn and the absorbable/biodegradable yarn comprises a multifilament yarn of a linear or polyaxial segmented copolyester containing repeat units derived from at least two monomers selected from the group consisting of glycolide, l-lactide, ε-caprolactone, and trimethylene carbonate.

27. The absorbable/biodegradable, fibrous composite construct as in claim 18 further comprising an additional biostable yarn comprising a polyethylene terephthalate multifilament yarn and the absorbable/biodegradable yarn comprises a multifilament yarn of a linear or polyaxial segmented copolyester containing repeat units derived from at least two monomers selected from the group consisting of glycolide, l-lactide, ε-caprolactone, and trimethylene carbonate.

28. The absorbable/biodegradable, fibrous composite construct as in claim 18 further comprising an additional biostable yarn comprising a polypropylene monofilament or multifilament yarn and the absorbable/biodegradable yarn comprises a multifilament yarn of a linear or polyaxial segmented copolyester containing repeat units derived from at least two monomers selected from the group consisting of glycolide, l-lactide, ε-caprolactone, and trimethylene carbonate.

29. The absorbable/biodegradable, fibrous composite construct as in claim 18 wherein the absorbable coating further comprises at least one bioactive agent selected from the group consisting of anti-inflammatory agents, anesthetic agents, antineoplastic agents, antimicrobial agents, microbicidal agents, antithrombic agents, and cell growth-promoting agents.

30. A absorbable/biodegradable, composite warp-knitted mesh comprising:

a fiber-reinforced interdependent, interlaced patterned mesh further comprising a biodegradable, segmented, polyaxial copolyester, the absorbable/biodegradable, composite warp-knitted mesh including a fiber reinforcement,
  i) the fiber reinforcement comprising less than 40 percent by weight of at least one biostable yarn comprising a multifilament yarn of ultrahigh molecular weight polyethylene and at least one absorbable/biodegradable yarn, and
  ii) wherein the at least one absorbable/biodegradable yarn comprises a heterochain polymer,
wherein the at least one biostable yarn and the at least one absorbable/biodegradable yarn assembled as initially interdependent, load-bearing components,
wherein the biodegradable, segmented polyaxial copolyester and biostable yarn interlace to form a mesh that defines intersections and voids between the biodegradable, segmented polyaxial copolyester and biostable yarn, and
wherein the biostable and biodegradable yarns transition during in vivo end-use to exhibit independent functional mechanical properties.

31. A absorbable/biodegradable, composite warp-knitted mesh as in claim 30 wherein the interdependent, interlaced pattern comprises from about 10 percent to about 40 percent by weight of the composite.

32. A absorbable/biodegradable, composite warp-knitted mesh as in claim 30 wherein the interdependent, interlaced pattern comprises from about 15 percent to about 50 percent by weight of the composite mesh.

33. A absorbable/biodegradable, composite warp-knitted mesh as in claim 30 wherein the biodegradable, segmented polyaxial copolyester of the interdependent, interlaced pattern comprises an amorphous, polyaxial, polymeric initiator end-grafted with a mixture of ε-caprolactone and at least one cyclic monomer selected from the group consisting of l-lactide, dl-lactide, glycolide, and trimethylene carbonate, such that crystallizable terminal segments are formed.

34. A absorbable/biodegradable, composite warp-knitted mesh as in claim 33 wherein the amorphous, polyaxial, polymeric initiator is formed by the ring-opening polymerization of trimethylene carbonate in the presence of a catalyst comprising stannous octanoate and a monocentric polyfunctional initiator selected from the group consisting of triethanolamine, trimethylolpropane, and pentaerythritol.

35. A absorbable/biodegradable, composite warp-knitted mesh as in claim 34 wherein the amorphous, polymeric initiator is formed by the ring-opening polymerization of a mixture of trimethylene carbonate and at least one monomer selected from the group consisting of p-dioxanone, ε-caprolactone, and 1,5-dioxepan-2-one.

* * * * *